United States Patent
Takaoka

(10) Patent No.: US 7,569,535 B2
(45) Date of Patent: Aug. 4, 2009

(54) 11-METHYL-13-TRIDECANOLIDE, 12-METHYL-14-TETRADECANOLIDE AND 13-METHYL-15-PENTADECANOLIDE, PERFUME COMPOSITIONS CONTAINING THE SAME, AND PROCESS FOR PRODUCTION OF COMPOUNDS INCLUDING THE SAME

(75) Inventor: Hideaki Takaoka, Noda (JP)

(73) Assignee: Soda Aromatic Co., Ltd. (JP)

( * ) Notice: Subject to any disclaimer, the term of this patent is extended or adjusted under 35 U.S.C. 154(b) by 309 days.

(21) Appl. No.: 11/579,173

(22) PCT Filed: Apr. 27, 2005

(86) PCT No.: PCT/JP2005/007961

§ 371 (c)(1),
(2), (4) Date: Oct. 30, 2006

(87) PCT Pub. No.: WO2005/105773

PCT Pub. Date: Nov. 10, 2005

(65) Prior Publication Data

US 2008/0020963 A1    Jan. 24, 2008

(30) Foreign Application Priority Data

Apr. 30, 2004    (JP) .............................. 2004-136437

(51) Int. Cl.
*A61K 8/00* (2006.01)
(52) U.S. Cl. ......................................... 512/11; 549/266
(58) Field of Classification Search .................. 512/11; 549/266
See application file for complete search history.

(56) References Cited

U.S. PATENT DOCUMENTS

| | | | |
|---|---|---|---|
| 3,907,831 A * | 9/1975 | Becker ........................ | 549/396 |
| 5,792,740 A * | 8/1998 | Mimoun et al. ............... | 512/11 |
| 5,831,101 A * | 11/1998 | Munro et al. ................ | 549/266 |
| 6,255,276 B1 | 7/2001 | Frater et al. | |

FOREIGN PATENT DOCUMENTS

| | | |
|---|---|---|
| CA | 1 221 105 A | 4/1987 |
| EP | 0 908 455 A1 | 4/1999 |
| JP | 54-8677 B2 | 4/1979 |
| JP | 10-204078 A | 8/1998 |
| JP | 11-193395 A | 7/1999 |
| JP | 2000-154394 A | 6/2000 |
| JP | 2002-275173 A | 9/2002 |

OTHER PUBLICATIONS

Syozo Abe, "Macrocyclic Musks, Part I: Review on Progress from Discovery up to Now," Koryo (1970), No. 96, pp. 19-27.
Daiyo Terunuma et al., "Optical Resolution of 3-Methyl-*N*-phenylglutaramic Acid and Synthesis of Optically Active Muscone," Journal of Organic Chemistry 1987, vol. 52, No. 8, pp. 1630-1632.
S. Arctander, "Perfume and Flavour Chemicals", 1969.

* cited by examiner

*Primary Examiner*—John R Hardee
(74) *Attorney, Agent, or Firm*—DLA Piper LLP (US)

(57) ABSTRACT

Among the compounds represented by the general formula (1),

[Formula 1]

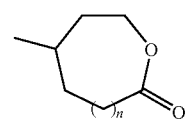

(in the formula, n is an integer of 7 to 13)
in particular, 11-methyl-13-tridecanolide of which n=8, 12-methyl-14-tetradecanolide of which n=9, and 13-methyl-15-pentadecanolide of which n=10 are novel compounds which have not been reported in prior art and the evaluation of the compounds for fragrance characteristics revealed that the compounds are macrocyclic lactone musks having not only strong fragrance of musk excellent in persistency but also fragrance characteristics like nitro musks. Furthermore, in the present invention, by containing at least one of those novel compounds, perfume compositions or perfume products having distinctive fragrance characteristics are obtained. The invention also provides a novel process for the production of compounds represented by the general formula (1).

5 Claims, No Drawings

11-METHYL-13-TRIDECANOLIDE, 12-METHYL-14-TETRADECANOLIDE AND 13-METHYL-15-PENTADECANOLIDE, PERFUME COMPOSITIONS CONTAINING THE SAME, AND PROCESS FOR PRODUCTION OF COMPOUNDS INCLUDING THE SAME

TECHNICAL FIELD

The present invention relates to 11-methyl-13-tridecanolide, 12-methyl-14-tetradecanolide and 13-methyl-15-pentadecanolide which have musk-like fragrances and are useful as perfume compounds, and have not been described in prior art. And, the present invention relates to perfume compositions in which at least one of these compounds is used. In addition, the present invention relates to a process for production of (ω-2)-methyl-alkanolide which includes these compounds and represented by the following general formula 1.

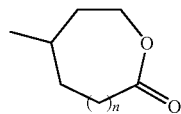

[Formula 1]

(in the formula, n denotes an integer of 7 to 13).

BACKGROUND ARTS

As widely known, musk-type perfume has been praised as an expensive perfume from ancient time, and with not only the elegant and fascinating fragrance but also with the high fixating effect which prevents diffusion of other volatile perfume compounds, it has been widely used as perfume for fragrances. In recent years, accompanying with the progress of chemical technology, the component of natural musk was isolated and its structure was determined, and chemical synthesis thereof has become possible. On the other hand, many compounds having musk-like fragrances which are not present in nature such as nitro musks or polycyclic musks were discovered and have been widely used as substitutes for those originated from animals or plants. Recently, accompanied by the increasing attention to diversified needs of consumer and safety of chemical substances, an expectation to macrocyclic musks with high biodegradability is growing and various new macrocyclic musk-type perfume compounds have been developed one after another.

As to the macrocyclic musks, it has been known for many years that $C_{14}$-$C_{16}$ lactones generally have musk-like fragrance. However, the fragrances of those lactones considerably differ in quality and intensity, and those which are practically valuable and commercially available are few such that only 3 or 4 compounds are mentioned. For example, as most popularly used one, 15-pentadecanolide or 11- (or 12-) pentadecen-15-olide is mentioned. In addition, according to nonpatent reference 1, 7-hexadecen-16-olide (paper 105) or 16-hexadecanolide (paper 923) are mentioned as valuable ones as substances of musk fragrance.

Moreover, in patent reference 1, processes for production of various $C_{14}$-$C_{17}$ lactones are described. In the patent reference 1, it is described that, in those lactones, the first or second position from cyclic oxygen may be substituted with a methyl group, or may have a double bond in the second or third position from the cyclic oxygen atom, and in those lactones, 15-methyl- and 14-methyl-pentadecanolide, etc., are also included. Those compounds were synthesized according to the production method of the above-mentioned 11- (or 12-) pentadecen-15-olide, but the patent reference 1 describes only that those compounds have an interesting fragrance, and does not indicate anything about a fragrance nature of the respective lactones.

And, in patent reference 2, it is described that many of saturated or unsaturated, unsubstituted or methyl substituted 14-17 cyclic members lactones are macrocyclic musk lactones. However, those lactones relate to a using method of ω-halogenated fatty acid which is a useful precursor thereof, and in the patent reference 2, no reference to the fragrance nature of the respective lactones is made.

And, in patent reference 3, too, it is described that 14-methyl-11-hexadecen-16-olide, 14-methyl-12-hexadecen-16-olide and 14-methyl-hexadecanolide are valuable perfume substances having strong and comfortable musk fragrances. However, the patent reference 3 only makes reference to the three compounds and it does not make any reference to similar species with different carbon number. According to the non-patent reference 2, as to the musk-like fragrance of the macrocyclic lactones, it is indicated that a strong musk-like fragrance is presented around the carbon number of 14 to 16, and it is also indicated that the musk-like fragrance is decreased in the macrocyclic lactone with carbon number 17, therefore, compounds of similar species with less carbon number are expected to have a stronger musk-like fragrance. Here, the production method of those compounds is, similar to the method of 11- (or 12-) pentadecen-15-olide, that in which cyclododecane is used as starting material.

Moreover, in patent reference 4, odorizing compositions containing various 15-17 cyclic member lactones are described. In the patent reference 4, it is described that, in those lactones, between the third position from cyclic oxygen atom and the fourth position from carbonyl group in general formula may be substituted with a methyl group, and may have a double bond between the third position from the cyclic oxygen atom and the third position from the carbonyl group. It is also describes that those compounds have a civet smell and often have a side note like a face powder, like a fruits and like a flowery odor. In the patent reference 4, it is described that several tens of compounds having the above-mentioned formula were actually obtained, together with their fragrance natures. According to that, the respective compounds have musk-like fragrances in common, but other than that, have side notes characteristic to them. That is, in perfume materials, change of fragrance nature based on a small structural difference is significant, and, as a result, it can be said that a value as a perfume material can be found only by actually preparing the compound and by smelling its fragrance.

As mentioned above, various studies have been made for the macrocyclic musks, but those actually being used in the perfume industry are only 3 or 4 compounds mentioned first. In order to respond to the diversified customer's needs, it is desired to develop novel macrocyclic musks having better fragrance characteristics.

Patent reference 1: JP-B-H54-8677
Patent reference 2: Specification of Canadian patent No. 1221105
Patent reference 3: JP-A-H10-204078
Patent reference 4: JP-A-H11-193395
Nonpatent reference 1: S. Arctander, Perfume and Flavour Chemicals
Nonpatent reference 2: Abe, Perfume Materials, 96, 19-27 (1970)

DISCLOSURE OF THE INVENTION

Problem(s) to be Solved by the Invention

In view of the present situation mentioned above, the present invention aims to respond to the needs of the perfume industry and the consumers for development of novel macrocyclic lactone musks having excellent fragrance characteristics. Moreover, it is desired that the process for producing them is easy.

The purpose of the present invention is to provide novel macrocyclic musks having a strong musk fragrance excellent in persistency and a process for producing the macrocyclic lactones. Another purpose of the present invention is to provide a perfume composition in which at least one of those compounds is used.

Means for Solving the Problem

I found that among the compounds represented by the general formula 1,

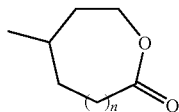

[Formula 2]

in particular, 11-methyl-13-tridecanolide of which n=8, 12-methyl-14-tetradecanolide of which n=9 and 13-methyl-15-pentadecanolide of which n=10, represented by the following chemical formulas, are novel compounds not reported in prior art, and that, as a result of a fragrance characteristic evaluation, they have not only a strong musk fragrance excellent in persistency but also have a nitro musk-like fragrance characteristic, and that they are macrocyclic lactone musks having a fragrance excellent in powdery feeling.

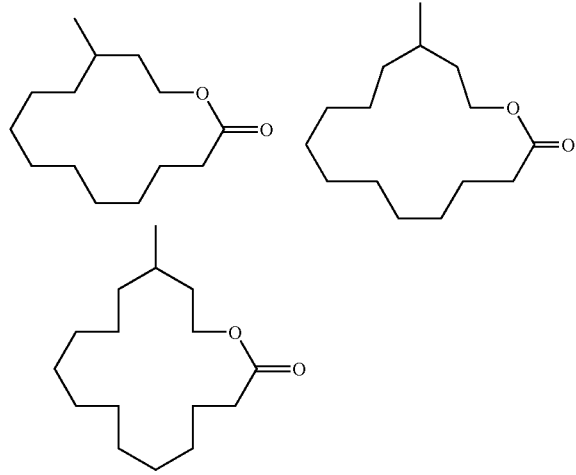

[Formula 3]

In addition, the present invention provides a perfume composition containing at least one species of those novel compounds and provides a process for production of the compound represented by the above-mentioned general formula 1.

Effect of the Invention

The macrocyclic lactones of the present invention, namely, 11-methyl-13-tridecanolide, 12-methyl-14-tetradecanolide and 13-methyl-15-pentadecanolide are novel compounds having a strong musk fragrance excellent in persistency. Furthermore, according to the process for production of the macrocyclic lactones of the present invention, those macrocyclic lactones can be produced safely and efficiently.

BEST MODE OF CARRYING OUT THE INVENTION

I found that,
2-methyl-2-(2-ω-alkoxycarbonylalkanoyl)-4-butanolide represented by the following general formula 4

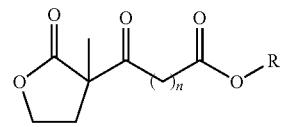

[Formula 5]

(in the formula, n denotes an integer of 7 to 13, R denotes an alkyl group or an alkenyl group) can be obtained by reacting a methylation agent to an alkali metal salt of 2-ω-alkoxycarbonylalkanoyl)-4-butanolide represented by the following general formula 3,

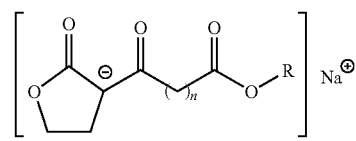

[Formula 4]

(in the formula, n denotes an integer of 7 to 13, R denotes an alkyl group or an alkenyl group) which is obtained by condensation reaction of γ-butyrolactone and a dicarboxylic ester represented by the general formula 2,

ROOC(CH$_2$)nCOOR (in the formula, n denotes an integer of 7 to 13, R denotes an alkyl group or an alkenyl group)

Moreover, I found that by hydrolysis and decarbonation of 2-methyl-2-(2-ω-alkoxycarbonylalkanoyl)-4-butanolide and successive conversion of carbonyl group of the obtained product into methylene group by a reduction reaction, long chain ω-hydroxy-(ω-2)-methyl-carboxylic acid represented by the following general formula 6.

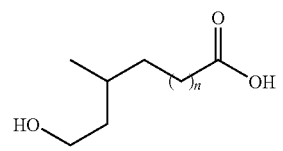

[Formula 6]

(in the formula, n denotes an integer of 7 to 13) can be obtained.

Furthermore, I found that, by intramolecular cyclization of long chain ω-hydroxy-(ω-2)-methyl-carboxylic acid, (ω-2)-methyl-alkanolide represented by the following general formula 1

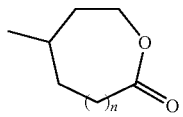
[Formula 7]

(in the formula, n denotes an integer of 7 to 13) can be obtained. Here, among those represented by the above-mentioned general formula 1, especially, 11-methyl-13-tetradecanolide, 12-methyl-14-tetradecanolide and 13-methyl-15-pentadecanolide represented by the following chemical formula, of which n=8 to 10 are novel compounds not reported in prior art.

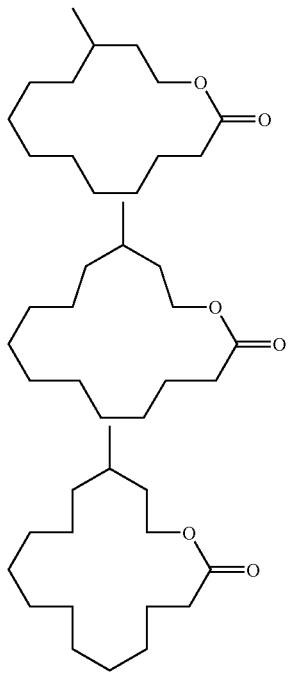
[Formula 8]

These novel macrocyclic lactones not only have a strong fragrance excellent in persistency, but they also are macrocyclic lactones which have nitro musk-like fragrance characteristic. And, they are useful compounds in the field of perfume industry.

In addition, the present invention provides a perfume composition containing at least one species of these novel compounds.

In the present invention, for synthesizing alkali metal salt of 2-(ω-alkoxy-carbonylalkanoyl)-4-butanolide, the method described in JP-A-H11-21283 which is our prior patent, can be adopted. That is, the alkali salt of 2-(ω-alkoxycarbonylalkanoyl)-4-butanolide can be obtained by a reaction between γ-butyrolactone and dicarboxylic acid ester under presence of a basic condensing agent.

As the condensing agent mentioned here, in general, condensation agents used in Claisen condensation or Dieckmann condensation of esters is used. For example, alkali metal such as a lithium, sodium, and potassium, alkali metal hydride such as lithium hydride, sodium hydride and potassium hydride, alkali-metal salt of ammonia such as lithium amide, sodium amide and potassium amide, alkali-metal amide of amines, such as lithium diisopropyl amide, sodium diisopropyl amide, lithium N-methyl anilide and sodium N-methyl anilide, alkali-metal alcoholate of alcohols such as sodium methoxide, sodium ethoxide, sodium n-propoxide, sodium isopropoxide, sodium n-butoxide, sodium t-butoxide, potassium t-butoxide, organoalkali metal compounds such as sodium naphthalene, and sodium triphenylmethyl, etc., are mentioned.

In the present invention, the condensing agent is preferably a metal alcoholate represented by the following general formula

ROM (in the formula, R denotes an alkyl group with 1 to 4 carbon atoms and M denotes an alkali metal).

And, in the present invention, the amount of the condensation agent to be used is not especially limited, but is preferably 0.1 to 5 equivalents per 1 molar γ-butyrolactone, more preferably, 0.5 to 3 equivalents. In addition, in the present invention, the amount of dicarboxylic acid ester to be used is preferably excessive mole per γ-butyrolactone, and 2 moles or more is especially preferable.

It is because, if the amount of dicarboxylic ester used is 2 moles or more, in particular, selectivity is improved. It is preferable to collect unreacted dicarboxylic acid ester from the reaction mixture, and recycle it into the condensation reaction for efficient reaction, and the collection of the unreacted dicarboxylic acid ester from the reaction mixture can be easily performed by simple distillation. Using excessive mole of dicarboxylic ester as well as the recycling makes a more efficient reaction possible. As the R of the dicarboxylic acid ester used in the present invention represented by the following general formula 2, ROOC(CH$_2$)nCOOR (in the formula, n denotes an integer of 7 to 13, and R denotes an alkyl group or an alkenyl group) an alkyl group or an alkenyl group, but for convenience of use, an alkyl group or an alkenyl group with 1 to 6 carbon atoms is preferably used. As examples of the R, methyl, ethyl, propyl, butyl, isopropyl, pentyl, hexyl, 2-ethy hexyl, octyl, allyl, 2-butenyl, 5-hexenyl, etc., are mentioned. In particular, R is preferably methyl group.

Next, 2-methyl-2-(2-ω-alkoxycarbonylalkanoyl)-4-butanolide of the present invention can be synthesized by directly reacting an alkylating agent to the reaction mixture of the alkali metal salt obtained as above-mentioned.

In the present invention, as alkylating agents, methyl halides such as methyliodide, methyl bromide and methyl chloride, or methane sulfonic acid ester, etc., are mentioned. The amount of the alkylating agent to be used is preferably 0.5-2 equivalents per γ-butyrolactone, more preferably, 0.7 to 1.2 equivalents. The reaction temperature is preferably, 40-140° C., and in view of the melting temperatures of metal salt and dicarboxylic acid ester as the starting material, 60-110° C. is more preferable.

Next, the process for production of (ω-2)-methyl-alkanolide which is the methyl macrocyclic lactone musk of the present invention is explained. By hydrolysis of 2-methyl-2-(2-ω-alkoxycarbonylalkanoyl)-4-butanolide obtained by the above-mentioned condensation reaction and methylation, simultaneously removing carbonyl carbon in lactone portion by decarbonate reaction, reducing carbonyl group of thus obtained reaction product into methylene group, and by intramolecular cyclization by esterification, (ω-2)-methylalkanolide can be easily obtained. The reaction process is the same as indicated by the following chemical reaction formula.

[Formula 9]

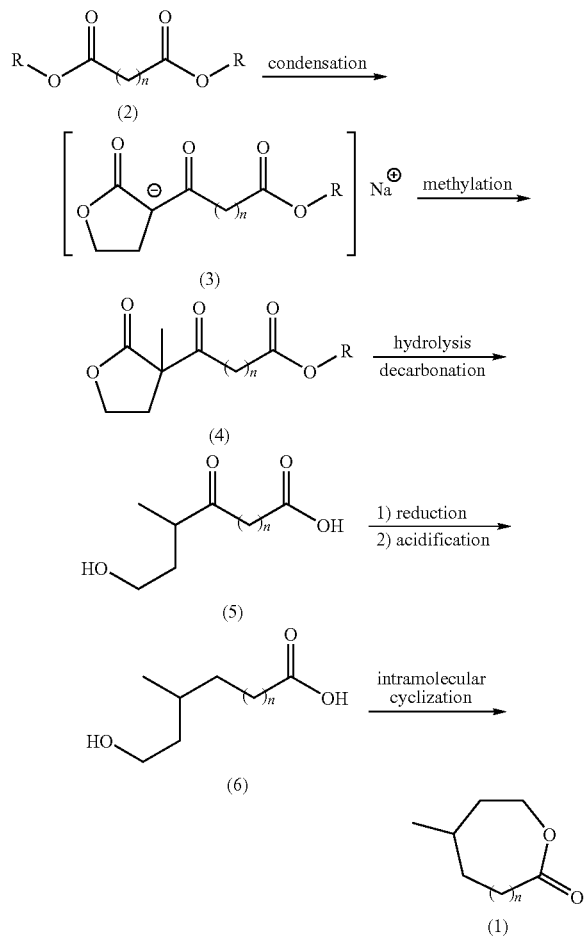

In the above chemical reaction formula, when the compound indicated by the above-mentioned general formula (4) (in the formula, n denotes an integer of 7 to 13, R denotes an alkyl group or an alkenyl group), namely, 2-methyl-2-(2-ω-alkoxycarbonylalkanoyl)-4-butanolide is hydrolyzed in an aqueous solvent by an alkaline base or acid, it is immediately hydrolyzed and decarbonated, and by the successive reduction of the obtained carbonyl group into methylene group, it is converted to a compound indicated by the general formula (5) (in the formula, n is an integer of 8 to 10, M is an alkali metal or an alkali earth metal). The carboxyl group of the compound shown by the above-mentioned general formula (5), which is an intermediate, is present in the solution in a form of a carboxylic salt when it is hydrolyzed by the alkaline base.

The alkaline base used in the hydrolysis of the compound represented by the above-mentioned general formula (4), is not especially limited as long as it can hydrolyze esters or lactones, but alkali hydroxide such as lithium hydroxide, sodium hydroxide and potassium hydroxide, alkali metal carbonates such as lithium carbonate and potassium carbonate, and alkali earth metal hydroxide such as barium hydroxide, can be used. And, as an acid, mineral acids such as sulfuric acid are preferably used. In addition, for converting the ketone in the compound shown by the above-mentioned general formula (5) into a methylene group, it is not especially limited as long as it is a publicly well known reduction reaction of ketone into methylene.

For example, in reactions with hydrazines including the improved Huang-Minlon method [Huang-Minlon, J. Am. Chem. Soc., 68 2487 (1946)] which are generally called as Wolff-Kishner reduction (David Todd, Organic Reactions, Vol 4, P378, John Wiley & Sons, 1948), once hydrazones are produced and the ketone is reduced to methylene in presence of a base.

It is not necessary to separate the hydrazones produced in the reaction system and it may be treated with the base.

As the base, alkali metal hydroxides such as sodium hydroxide or potassium hydroxide, alkali metal carbonates such as sodium carbonate or potassium carbonate, alkali metal aluminates such as sodium aluminate or potassium aluminate, alkali metal phosphates such as sodium phosphate or potassium phosphate, alkali metal acetates such as sodium acetate, potassium acetate, and alkali metal alcoholate such as sodium methoxide, can be used.

As the reduction temperature, 150 to 250° C. is preferably applied. The hydrazines may be used in the amount of one mole or more to one mole of the compound shown in the above-mentioned general formula (4). The amount to be used is preferably one to three moles. As the hydrazines to be used, hydrazine monohydrate, hydrazine sulfate, etc., are preferably used.

Another method for reducing ketone to methylene is a reduction by zinc or zinc amalgam with acid which is generally called as Clemmensen reduction [E. L. Martin, Organic Reactions, Vol 1, P155, John Wiley & Sons (1942)]. In the present invention, the reduction by hydrazines is most preferably used.

Here, in order to convert the compound indicated in the above-mentioned general formulas (4) to (6) into ω-hydroxy-(ω-2)-carboxylic acid, it is possible that the compound after the hydration or the reaction mixture containing the carboxylic acid salt is subjected to the following ketone reduction reaction as it is, without separating or isolating the intermediate compound, to produce ω-hydroxy-(ω-2)-methylcarboxylic acid. However, the compound of the above-mentioned general formula 3 is a compound capable of being isolated. Let me explain with an example, after the compound of the above-mentioned general formula (4) is subjected to hydrolysis and decarbonation in an aqueous alkali liquid (at this time, the compound of the above-mentioned general formula (5) is present in a form of alkali metal salt of carboxylic acid) to make a reaction mixture, hydrazines were added to produce hydrazones, and then the temperature is elevated to a temperature required for the ketone reduction, to thereby carry out a reduction reaction in a presence of the base and an alkaline base solution of the compound indicated by the above-mentioned general formula (6) is obtained. When this liquid is returned to acidic state, ω-hydroxy-carboxylic acid is isolated. As a matter of course, the present invention is not limited to the method mentioned here.

In addition, as to the compound indicated in the above-mentioned general formula (6), it is not necessary to isolate it for reaction, and by an intramolecular cyclization to convert it to a lactone by a high dilution method, a polymerization-depolymerization method or an intramolecular ester change as it is a reaction mixture, macrocyclic lactone compounds can be easily obtained.

Next, the present invention is explained with reference to examples. However, the following examples are shown only for exemplifications and in any means, the present invention should not be understood in a limited way.

EXAMPLES

Example 1

Synthesis of 12-methyl-14-tetradecanolide 11-undecanedioic acid dimethyl ester (1057 g, 4.33 mmols) was put into a reactor, heated and stirred under a reduced pressure of 80 kPa at 105° C. The mixture of γ-butyrolactone (92.6 g, 1.08 mols) and 28% by weight of sodium methoxide solution in methanol (207.64 g, 1.08 mols) prepared at the room temperature was dropped into the heated 11-undecanedioic acid dimethyl ester in 30 minutes while methanol was distilled off. After continuing the reaction for 30 minutes then, the pressure was reduced to 26.7 kPa and the reaction was continued for 240 minutes.

Next, after returning to ordinary pressure, the reactant was cooled to 70° C. and, while being stirred, methyliodide (145.5 g, 1.024 mols) was dropped into it in 30 minutes. N-hexane (700 g) was poured into it and insoluble substance was removed by filtration. N-hexane in the filtrate was distilled off under a reduced pressure. The remaining oily substance was subjected to a distillation under a reduced pressure (oil bath temperature 200° C./60 to 130 Pa) and excessive 11-undecanedioic acid dimethyl ester was distilled off. 790.8 g of the distilled substance and 206.6 g of the distillation residue were obtained.

As a result of an analysis of the distillation residue by gas chromatography, it was found that 88.8% by weight of the compound indicated by the general formula (2) (n=9, R=Me) was contained. This was mixed with aqueous solution of 5% sodium hydroxide (111g) and heated/refluxed for 5.5 hours. After diethylene glycol (283 g) and 60% hydrazine monohydrate (105 g) were dropped into the reaction liquid and stirred for one hour at 110° C., the temperature of the reaction system was elevated to 170 to 200° C. while removing water, and after aqueous solution of 30% sodium hydroxide (86 g) was dropped into it in 4 hours, it was stirred for 6 hours at that temperature. While pouring water (1000 g) into it, it was cooled, and with addition of diluted sulfuric acid it was extracted with toluene. After the organic layer was washed with water, the solvent was removed under a reduced pressure, and 126 g of a crystalline residue containing 12-methyl-14-hydroxytetradecanoic acid (n=9) as the main component was obtained. This was cyclized by intramolecular ester interchange reaction to thereby obtain 82.7 g of a cyclic compound. This contained 99.2% by weight of 12-methyl-14-tetradecanolide. The yield was 32 mol %/butyrolactone.

1H-NMR (CDCl3, 400 MHz) 4.15 (2H)m; 2.33 (2H)m; 0.90 (3H)d J=6.4 Hz 13C-NMR (CDCl3) 174.05; 62.15; 36.13; 33.83; 33.70; 27.53; 27.42; 26.55; 26.53; 26.25; 26.21; 25.45; 24.65; 24.53; 19.55 IR(film) 2925; 2860; 1735; 1455; 1345; 1235; 1173; 1145; 1115 MS 240(5); 222(6); 211(9); 193(22); 175(8); 152(8); 127(12); 110(16); 97(32); 83(40); 70(100); 55(69); 41(41)

Fragrance; It has a strong fragrance, characterized to be nitro musk-like (strong Musk Ambrett-like nuance). As to fragrance quality, it is excellent in musky impression, sweetness and powdery impression.

Example 2

Synthesis of 11-methyl-13-tridecanolide 1,10-decanedioic acid dimethyl ester (750 g, 3.26 mols) was put into a reactor, heated and stirred under a reduced pressure of 80 kPa at 105° C. A mixture of γ-butyrolactone (70.1 g, 0.82 mol) and 28% by weight of sodium methoxide solution in methanol (157.2 g, 0.82 mols) prepared at the room temperature was dropped into the heated 1,10-decanedioic acid dimethyl ester in 30 minutes while methanol was distilled off. After continuing the reaction for 30 minutes then, the pressure was reduced to 26.7 kPa to further continue the reaction for 240 minutes.

Next, after returning to ordinary pressure, the reactant was cooled to 70° C. and, while being stirred, methyliodide (124.3 g, 0.815 mol) was dropped into it in 30 minutes. N-hexane (350 g) and, next, water (750 g) were poured into it. After removing the water layer, it was washed with water (300 g: twice). N-hexane was distilled off under a reduced pressure and 777 g of an oily substance was obtained. The oily substance was subjected to a distillation under a reduced pressure (oil bath temperature 200° C./60 to 130 Pa) and excessive 1,10-decanedioic acid dimethyl ester was distilled off. 568.6 g of a distilled substance and 206.8 g of a distillation residue were obtained.

As a result of an analysis of the distillation residue by gas chromatography, it was found that 78.7% by weight of the compound indicated by the general formula (2) (n=8, R=Me) was contained. This was mixed with aqueous solution of 10% sodium hydroxide (564 g) and heated/refluxed for 5.5 hours. After diethylene glycol (200 g) and 60% hydrazine monohydrate (112 g) were dropped into the reaction liquid and stirred for one hour at 110° C., the temperature of the reaction system was elevated to 170 to 200° C. while removing water, and after aqueous solution of 30% sodium hydroxide (89 g) was dropped into it in 4 hours, it was stirred for 6 hours at that temperature. While pouring water (800 g) into it, it was cooled, and with addition of diluted sulfuric acid it was extracted with toluene. After the organic layer was washed with water, the solvent was removed under a reduced pressure, and 158 g of a crystalline residue containing 11-methyl-13-hydroxytridecanoic acid (n=8) as the main component was obtained. This was cyclized by intramolecular ester interchange reaction to thereby obtain 71.4 g of a cyclic compound. This contained 99.6% by weight of 11-methyl-13-tridecanolide. The yield was 38 mol %/butyrolactone.

1H-NMR (CDCl3, 400 MHz) 4.19 (2H)m; 2.37 (2H)m; 0.90 (3H)d J=6.9 Hz 13C-NMR (CDCl3) 173.82; 61.73; 35.65; 34.19; 32.26; 26.10; 25.64; 25.43; 25.33; 24.25; 24.20; 23.94; 23.87; 19.43 IR(film) 2925; 2860; 1735; 1455; 1375; 1255; 1165; 1100 MS 226(3); 208(4); 197(9); 179(21); 127 (13); 111(14); 97(28); 83(37); 70(100); 55(68); 41(40)

Fragrance; It has a strong fragrance, and its nitro musk-like (Musk Ambrett-like nuance) characteristic is quite similar to that of 12-methyl-14-tetradecanolide. It has voluminous and powdery impressions similar to those of 12-methyl-14-tetradecanolide, although they are a little weak.

Example 3

Synthesis of 13-methyl-15-pentadecanolide 1,12-dodecanedioic acid dimethyl ester (1000.0 g, 3.87 mols) was put into a reactor, heated and stirred under a reduced pressure of 80 kPa at 105° C. Methanol was distilled off while the mixture of γ-butyrolactone (83.3 g, 0.97 mol) and 28% by weight of sodium methoxide solution in methanol (186.7 g, 0.97 mols) prepared at the room temperature was dropped into the heated 1,12-dodecanedioic acid dimethyl ester in 30 minutes. After continuing the reaction for 30 minutes then, the pressure was reduced to 26.7 kPa to further continue the reaction for 240 minutes.

Next, after returning to ordinary pressure, the reactant was cooled to 70° C. and, while being stirred, methyliodide (137.7 g, 101.6 mols) was dropped into it in 30 minutes. N-hexane (700 g) and, next, water (3009) were poured into it. After removing the water layer, it was washed with aqueous solution of 10% sodium hydroxide (150 g: twice) and water (200.0 g: twice). N-hexane was distilled off under a reduced pressure. The remained oily substance was subjected to a distillation under a reduced pressure (oil bath temperature 200° C./60 to 130 Pa) and excessive 1,12-dodecanedioic acid dimethyl ester was distilled off. 762.9 g of a distilled substance and 264.2 g of a distillation residue were obtained.

As a result of an analysis of the distillation residue by gas chromatography, it was found that 80.7% by weight of the compound indicated by the general formula (2) (n=10, R=Me) was contained. This was mixed with aqueous solution of 10% sodium hydroxide (675 g) and heated/refluxed for 5.5 hours. After diethylene glycol (230 g) and 60% hydrazine monohydrate (124 g) were added to the reaction liquid and stirred for one hour at 110° C., the temperature of the reaction system was elevated to 170 to 200° C. while removing water, and after aqueous solution of 30% sodium hydroxide (100 g) was dropped into it in 4 hours, it was stirred for 6 hours at that temperature. While pouring water (930 g) into it, it was cooled, and with addition of diluted sulfuric acid it was extracted with toluene. After the organic layer was washed with water, the solvent was removed under a reduced pressure, and 254 g of a crystalline residue containing 13-methyl-15-hydroxypentadecanoic acid (n=10) as the main component was obtained. This was cyclized by intramolecular ester interchange reaction to thereby obtain 80.7 g of a cyclic compound. This contained 98.9% by weight of 13-methyl-15-pentadecanolide. The yield was 32 mol %/butyrolactone.

1H-NMR (CDCl3, 400 MHz) 4.16 (2H)m; 2.32 (2H)m; 0.90 (3H)d J=6.4 Hz 13C-NMR (CDCl3) 173.89; 61.86; 35.31; 34.49; 34.20; 30.82; 27.68; 27.25; 26.57; 26.42; 26.26; 26.10; 25.87; 24.89; 24.52; 19.51 IR(film) 2930; 2860; 1740; 1460; 1350; 1245; 1173; 1115 MS 254(5); 236(9); 225(11); 207(21); 111(16); 97(35); 83(42); 70(100); 55(68); 41(40)

Fragrance; In quality, it has an elegance like that of 15-pentadecanolide and a nitromusk-like characteristic similar to that of 12-methyl-14-tetradecanolide.

INDUSTRIAL APPLICABILITY

The macrocyclic lactones of the present invention, namely, 11-methyl-13-tridecanolide, 12-methyl-14-tetradecanolide and 13-methyl-15-pentadecanolide are novel compounds having a strong musk fragrance excellent in persistency. They are extremely useful compounds as musk-like perfume materials. Furthermore, according to the process for production of the macrocyclic lactones of the present invention, these novel macrocyclic lactones can be produced safely and efficiently.

The invention claimed is:
1. 11-methyl-13-tridecanolide.
2. 12-methyl-14-tetradecanolide.
3. 13-methyl-15-pentadecanolide.
4. A mixture of 11-methyl-13-tridecanolide, 12-methyl-14-tetradecanolide and 13-methyl-15-pentadecanolide.
5. A perfume composition characterized by containing at least one compound selected from the group consisting of the compounds described in claims 1 to 3.

* * * * *